United States Patent [19]
Lyman et al.

[11] Patent Number: 4,824,642
[45] Date of Patent: Apr. 25, 1989

[54] MULTI-CHANNEL PIPETTER

[75] Inventors: George Lyman, Rocky Point; Gregory Mathus, Concord, both of Mass.

[73] Assignee: Costar Corporation, Cambridge, Mass.

[21] Appl. No.: 921,319

[22] Filed: Oct. 21, 1986

[51] Int. Cl.⁴ .............................................. G01N 1/14
[52] U.S. Cl. ..................... 422/100; 436/809; 435/293; 73/863.32; 73/864.13; 73/864.14; 73/864.17; 73/864.18
[58] Field of Search ......................... 422/100; 435/293; 73/863.32, 864.13, 864.14, 864.16, 864.17, 864.18; 436/809

[56] References Cited

U.S. PATENT DOCUMENTS

| | | | |
|---|---|---|---|
| 3,656,351 | 4/1972 | Raczak | 73/864.18 |
| 3,754,687 | 8/1973 | Norton | 73/864.18 |
| 3,827,305 | 8/1974 | Gibson et al. | 73/864.18 |
| 3,975,960 | 8/1976 | Croslin | 73/864.18 |
| 4,096,751 | 6/1978 | Wilhers et al. | 73/864.18 |
| 4,237,095 | 12/1980 | Suovaniemi et al. | 73/864.18 |
| 4,257,268 | 3/1981 | Pepicelli et al. | 73/864.17 |
| 4,466,298 | 8/1984 | Tervamaki et al. | 422/100 |
| 4,599,220 | 7/1986 | Yonkers et al. | 73/864.17 |

FOREIGN PATENT DOCUMENTS

| | | | |
|---|---|---|---|
| 2504269 | 1/1976 | Fed. Rep. of Germany | 422/100 |
| 51403 | 6/1966 | Poland | 73/425.6 |

Primary Examiner—Barry S. Richman
Assistant Examiner—Lynn M. Kummert
Attorney, Agent, or Firm—Wolf, Greenfield & Sacks

[57] ABSTRACT

A multi-channel pipetter has a U-shaped housing with horizontal upper and lower arms and an interconnecting hand grip portion. A plurality of nozzles that serve to support replaceable tips are mounted on the lower arm in a vertical orientation and are connected by a flexible tubing that extends upwardly through the grip portion to a circular array of cylinders disposed horizontally in the upper arm. A piston-cylinder-volume setting mechanism is horizontally disposed in the upper arm. The mechanism is actuated by a trigger on the hand grip portion and the volume is controlled by a micrometer head which operates a stop within the upper arm. A tip ejector is mounted in the lower arm which provides substantial mechanical advantage for stripping the tips from the nozzles.

20 Claims, 5 Drawing Sheets

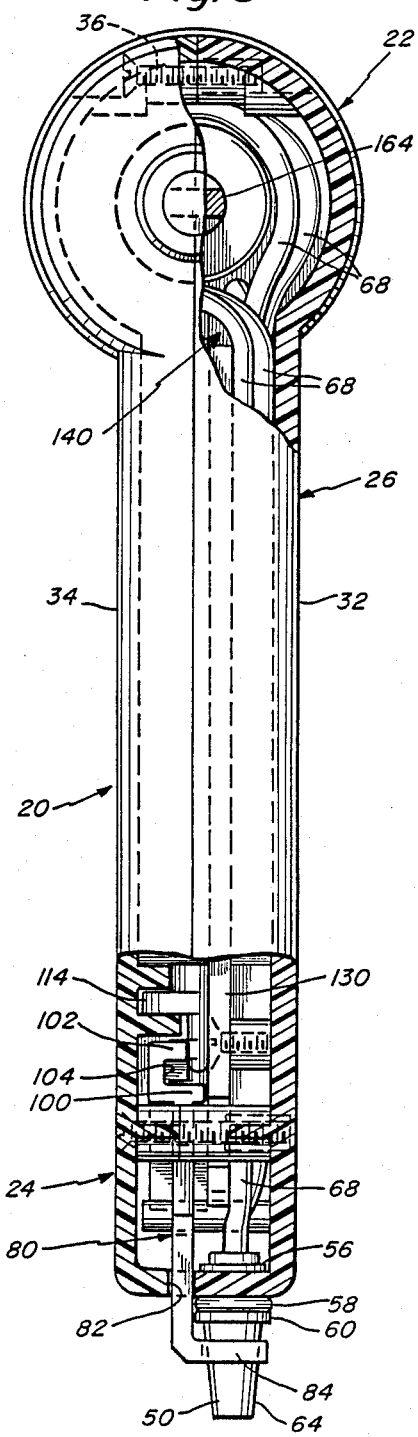
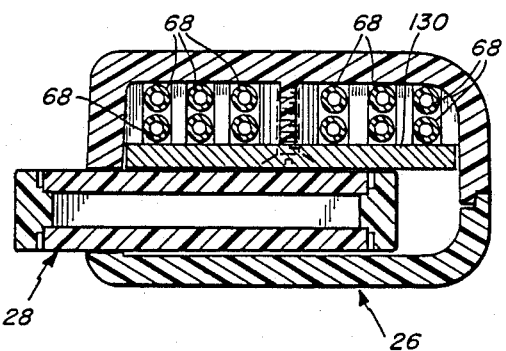
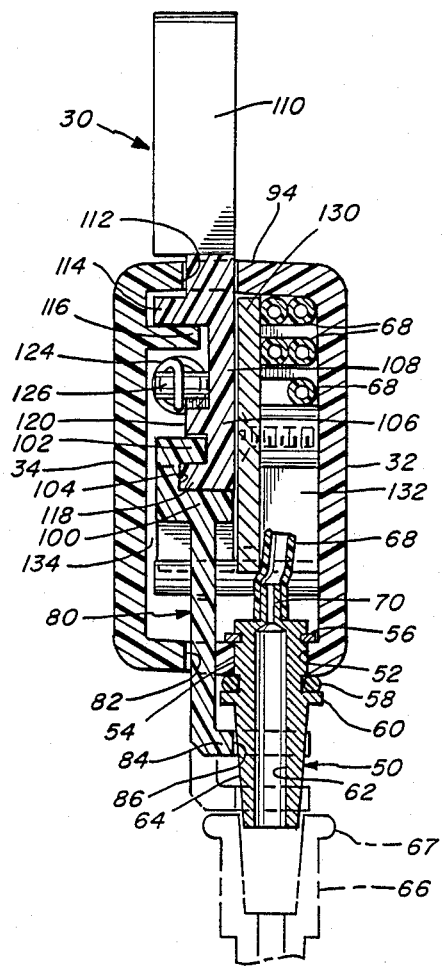

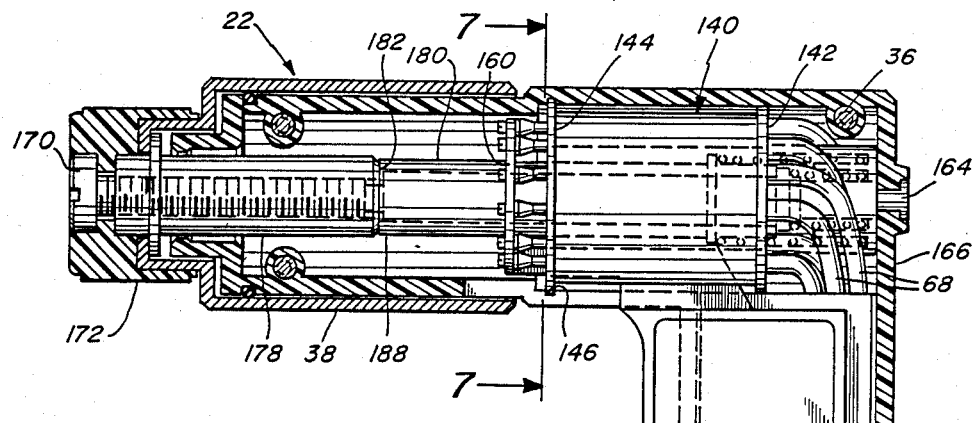
Fig. 6
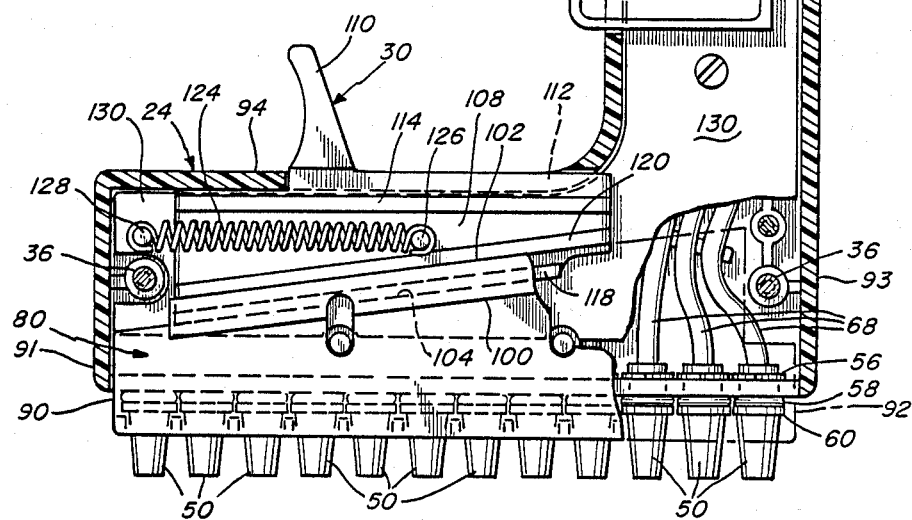
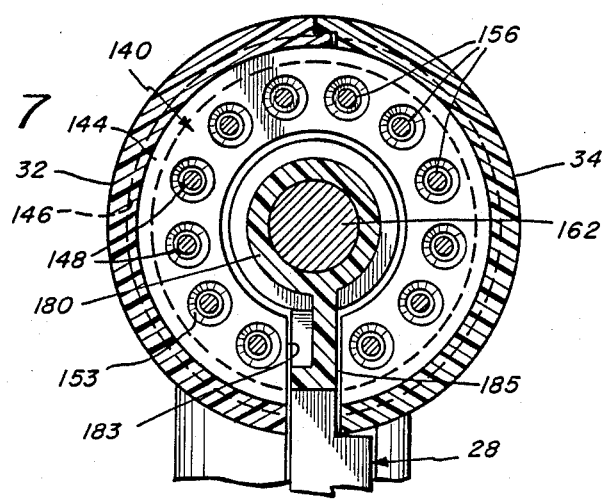
Fig. 7

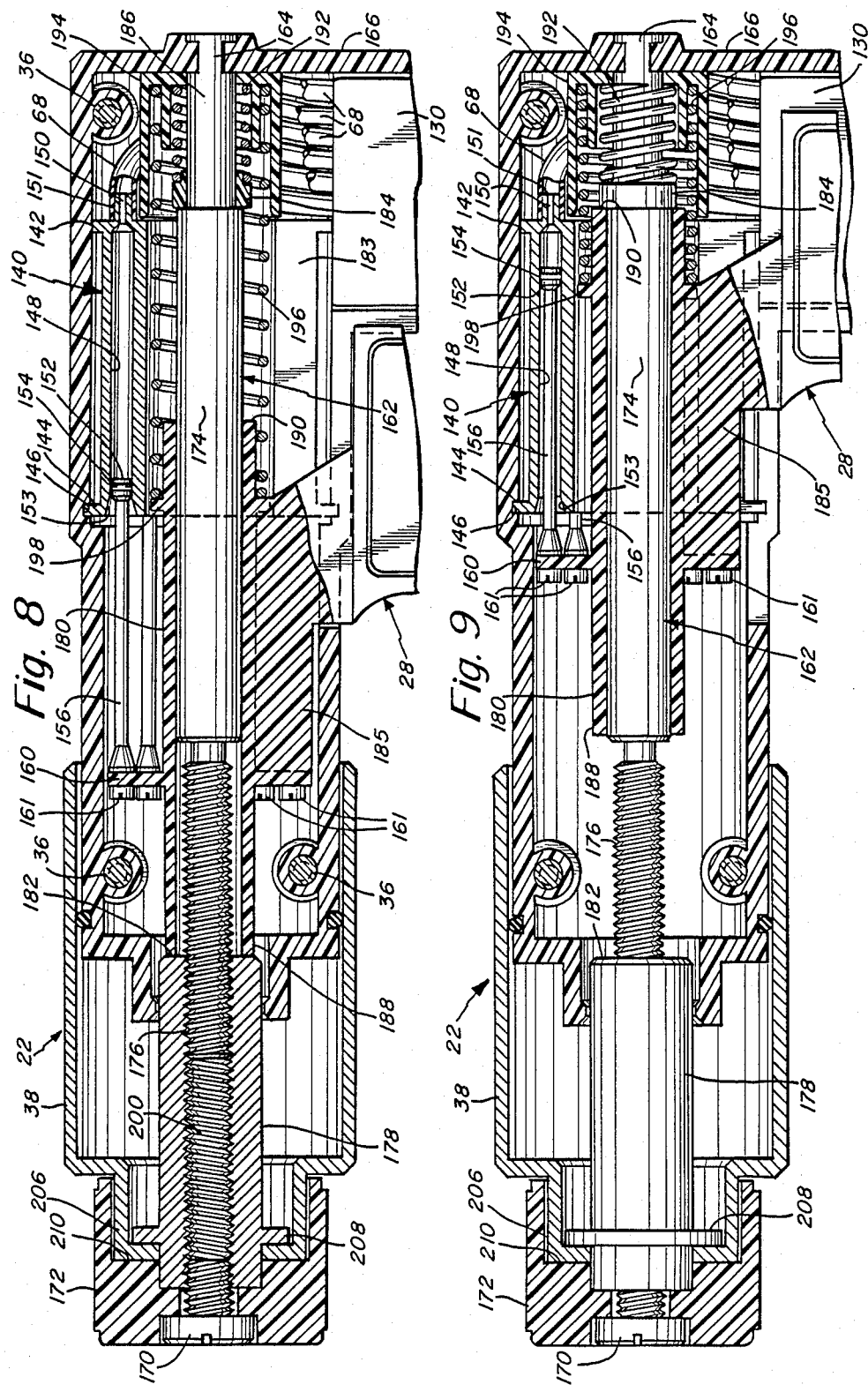

MULTI-CHANNEL PIPETTER

INTRODUCTION

This invention relates to laboratory pipettes and more particularly comprises a new and improved adjustable volume multi-channel pipetter designed for laboratory use. The pipetter is particularly designed to fill the wells of multi-well plates that are used for a variety of tests and experiments.

The presently available adjustable volume, multi-channel, hand-held pipetting device for laboratory use includes a row of twelve metering cylinders oriented vertically and controlled by a vertically movable piston assembly disposed above the cylinders. A handle extends vertically above the piston assembly, and the handle in turn carries a vertically movable plunger connected to the piston assembly so that the piston assembly may be moved to fill and dispense fluid from the metering cylinders. The stroke of the plunger is adjustable so as to vary the volume of fluid transferred by the device.

The prior product has several disadvantages. First, the instrument is too tall to be used comfortably under a laminar airflow hood which is commonly used in performing sterile laboratory procedures. Second, the instrument cannot be autoclaved. If it becomes contaminated with dangerous organisms, it may be necessary to discard the entire unit. Third, both hands are required to eject the disposable tips which are connected to the metering cylinders. Fourth, the tip ejector does not work effectively. The device does not provide any mechanical advantage in the ejector mechanism and consequently, when tips are pressed onto the bottoms of the metering cylinders firmly enough so as not to leak, the mechanism cannot always eject the tips. Rather, the tips must be removed separately by hand, or by using pliers on the mechanism. Fifth, there is a considerable variation in volumetric accuracy and repeatability from one metering cylinder to another. The straight, long piston assembly is subject to racking and deflection, and a certain amount of looseness must be built into the assembly to provide the necessary clearances. Sixth, the prior art device described above employs a mechanical rotation for setting the plunger stroke, and it is not possible to set fractional values between the numbers on the counter. Seventh, repeated use of the instrument causes fatigue, and the poor human engineering of the device also makes it difficult to aim the tips into small wells because its handle lacks orientation and the hand holding the instrument is very remote from the tips.

A multi-channel pipetter presently offered to the market under the trademark OCTOPETTE is manufactured by Costar Corporation, the assignee of the present application. The OCTOPETTE is disclosed in U.S. Pat. No. 4,599,220 dated July 8, 1986. While the human engineering and size of that unit makes it substantially more convenient than the adjustable volume instrument described above, the latter pipetter is not adjustable but rather is offered in four different models for different dispensing volumes. Furthermore, the accuracy of the device is not adequate for certain applications. The present invention overcomes the limitations and disadvantages of the prior art instruments. The vertical in line design of the prior art adjustable pipetter is avoided and in its place, the metering cylinders are oriented horizontally in the housing of the instrument. The pistons and volume setting mechanism are also arranged horizontally, which reduces the overall height of the pipetter by several inches. The material selection for the manufacture of the present invention is limited to those which can withstand repeated autoclaving at 250° Fahrenheit. Several of the metal parts of the instrument are machined from stainless steel or aluminum.

The pipetter includes a tip ejector that provides a very substantial mechanical advantage and which also can be operated with the same hand that holds the instrument. This allows convenient use of the device and enables the ejector to remove tips that are wedged very tightly onto the tip holders. Volumetric accuracy of the present invention is exceptionally high. Of substantial importance is the elimination of the long piston support of the prior art and its replacement with a circular array of cylinders centered around a rigid, precision ground, steel guide rod. For accurate metering, a micrometer arrangement is used which affords accurate setting between numbers on the micrometer scale. It also facilitates quick setting of the instrument and enables the instrument to be zeroed with ease.

The instrument of the present invention may be used repeatedly for hours because of the good ergonomic design. The handle is of a pistol grip configuration which also facilitates accurate aiming of the tips.

The present invention is embodied in a generally U-shaped housing having lower and upper horizontal arms joined at one end by a grip portion. The lower arm carries an array of aligned nozzles that serve as tip holders for the instrument. The upper arm carries a horizontally positioned cylinder block within which are arranged a circular array of cylinders close to the cylinder block axis. The cylinder block is coaxial with a rigid, precision machined guide rod on which a sleeve is slidably mounted. The sleeve is connected to an array of piston rods that carry the pistons in the cylinders. The sleeve in turn is actuated by a primary trigger that extends from the front of the grip portion of the housing. An adjustable stop is coaxial with the sleeve, and a micrometer assembly having a rotatable barrel, scales, and index line are externally disposed on the upper arm for easy and accurate setting of the stop. The stop controls the length of the stroke of the sleeve by which metering is achieved.

A tip ejector including a secondary trigger is horizontally movable on the lower arm of the housing, and an ejector plate is vertically movable in the lower arm. A cam arrangement connects the secondary trigger and the ejector plate to provide a very substantial mechanical advantage so that ease of operation is assured.

This invention will be better understood and appreciated from the following detailed description read in connection with the accompanying drawings.

BRIEF FIGURE DESCRIPTION

FIG. 3 is a rear elevation view of the pipetter, with parts broken away;

FIG. 4 is a horizontal cross-sectional view of the pipetter taken along section line 4—4 of FIG. 1, through the grip portion of the pipetter housing;

FIG. 5 is a vertical cross-sectional view taken along the section line 5—5 of FIG. 1, through the lower arm of the pipetter housing;

FIG. 6 is a cross-sectional view of the pipetter with certain parts broken away, showing the various parts of the device assembled within the pipetter housing;

FIG. 7 is a vertical cross-sectional view taken along the section line 7—7 of FIG. 6, through the upper arm of the pipetter;

FIGS. 8 and 9 are vertical cross-sectional views of the upper arm of the pipetter showing the trigger in its released and retracted positions, respectively.

DETAILED DESCRIPTION

Figure 1:
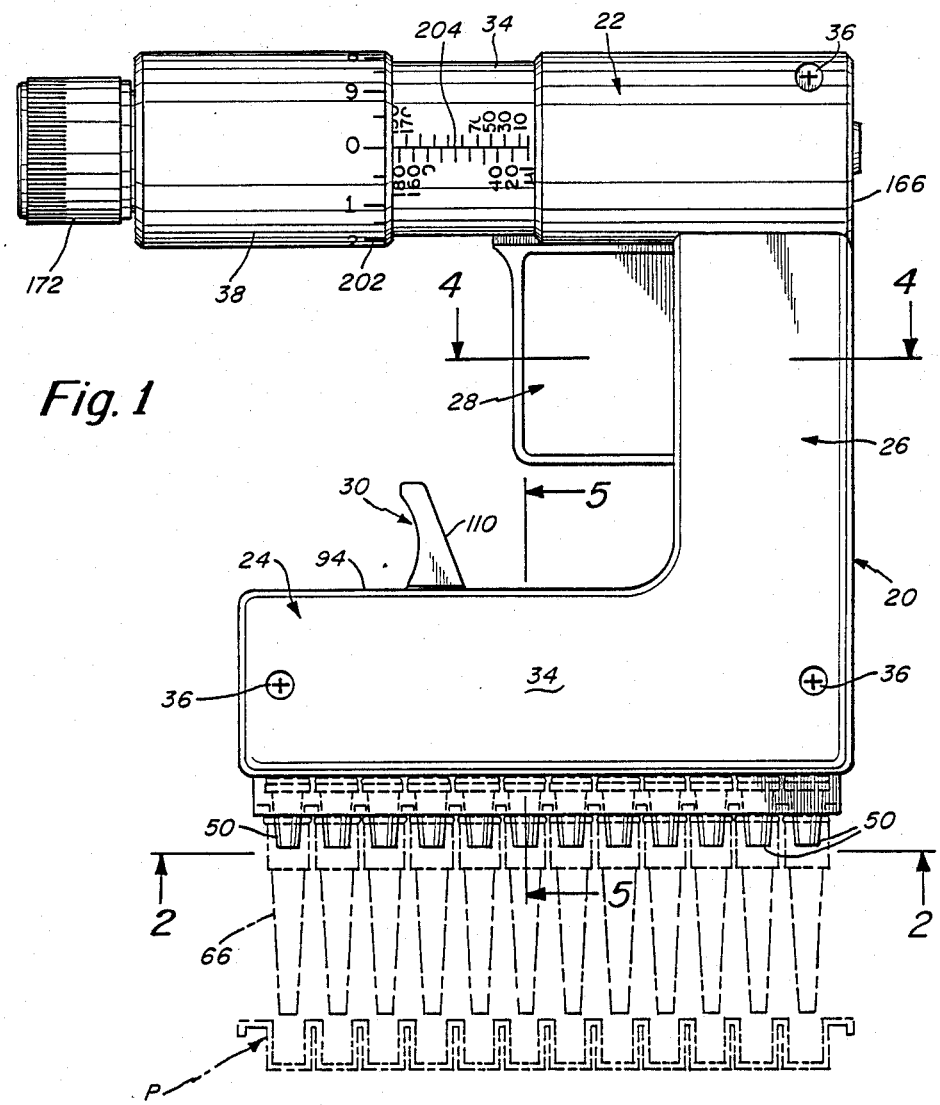
FIG. 1 is a side elevation view of a multi-channel pipetter constructed in accordance with this invention.
Figure 2:
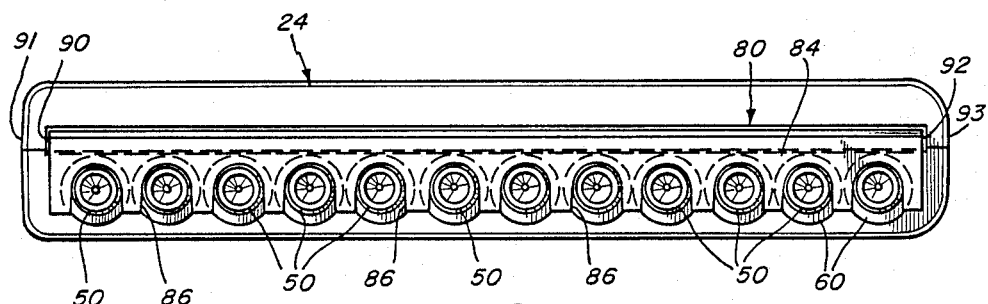
FIG. 2 is a bottom plan view of the pipetter viewed along the sight line 2—2 in FIG. 1 looking at the lower ends of the tip holders.

The multi-channel pipetter of this invention shown in the drawing includes a housing 20 having upper and lower horizontal arms 22 and 24 connected by a grip portion 26. A main trigger 28 is disposed between the upper and lower arms 22 and 24 of the housing and may be retracted into the grip portion 26 to operate the pipetter. A secondary trigger 30 is carried on the upper side of the lower arm 24 and controls a stripper mechanism for removing disposable tips that are mounted on tip holders. The housing 20 includes rear, and front bodies 32 and 34 which are held together by a number of screws 36 and a barrel 38 which forms part of the volume adjustment assembly. All of the various parts of the instrument are described in detail below.

Lower arm 24 of the pipetter carries 12 tip holders 50 in the form of nozzles, which are seated in openings 52 provided in the lower wall 54 of the rear body 32 (see FIGS. 3 and 5). Each of the tips is held in place by a retainer ring 56 disposed inside the lower arm 24 and an 0-ring 58 disposed outside the arm against the lower wall 54. The O-rings 58 are in turn seated in shallow recesses provided in the tip holders and defined on one side by the flanges 60. Each of the tip holders has an axial passage 62. Each tip holder also is provided with a tapered outer surface 64 onto which a disposable tip may be mounted and be secured in place by the matching tapers of the holder and tip respectively. The disposable tips 66 are suggested by broken lines in FIGS. 1 and 5. The O-rings 58 provide an important advantage to the pipetter. When a row of twelve pipette tips 66 is disposed in a rack from which they are to be picked up by the tip holders 50, there may be some variation in the tip heights and/or there may be deflection in the rack which supports them. The 0-rings 58 impart vertical compliance to each tip holder 50 so that they may accommodate the tolerance variations and still pick up the tips. This is a problem that is especially evident in eight and twelve channel pipetters.

As suggested in FIGS. 3, 5 and 6, each of the tip holders is connected at its top to a length of flexible tubing 68 which may be slipped onto the upper projection 70 of the tip holder body. The passage 62 through each tip holder communicates with the tubing 68. The upper end of each length of tubing 68 is in turn connected to one of the cylinders in the cylinder block 140 in the upper arm 22 of the pipetter, which is described in detail below.

In FIGS. 5 and 6, a stripper plate 80 is shown disposed in the lower arm 24 of housing 20. The stripper plate extends out of the lower arm 24 through a slot 82 in bottom wall 54 between the mating edges of the rear and front bodies 32 and 34. The lower end of the stripper plate 80 carries a foot 84 that extends from the bottom of the vertical portion of the stripper plate toward the tip holders 50. The foot 84 of stripper plate 80 actually surrounds a major portion of the circumference of each tip holder 50 by virtue of the slot 86 in the foot 84.

The stripper plate 80 is free to move vertically up and down in the housing 20. It is guided by the cooperation of the vertical side edges 90 and 92 of the stripper plate with the closely adjacent walls 91 and 93 of the lower arm 24 of housing 20 (see FIG. 6). The stripper plate is actuated by the secondary trigger 30 disposed immediately above the upper wall 94 of the lower arm 24 of housing 20.

The stripper plate 80 includes as an integral part thereof a pair of parallel flanges 100 and 102 (see FIGS. 3 and 5) that extend upwardly and to the right as viewed in FIG. 6 in the direction of the grip portion 26. The flanges along with the slot 104 between them form a hook-like connection with the lower end 106 of the extension 108 of trigger 30, that is disposed inside the lower arm 24 of housing 20. The upper portion 110 of the secondary trigger 30, which is exposed above the lower arm 24, is connected to the extension 108 through a slot 112 formed between the mating edges of the upper wall 94 of the lower arm. The trigger 30 is supported in place but permitted to slide horizontally on the lower arm by virtue of the engagement of the flange 114 on the trigger extension 108 with flange 116 formed as an integral part of the front body 34 (see FIG. 5). The lower portion 106 of the trigger extension 108 also carries a pair of flanges 118 and 120 that cooperate with the flanges 100 and 102 and the slot between them to form the hook-like connection between the trigger 30 and stripper plate 80. The flanges 118 and 120 are inclined to the horizontal as viewed in FIG. 6 so as to match and mate with the flanges 100 and 102.

The trigger 30 is biased to the forward or left position shown in FIG. 6 by coil spring 124 connected at one end to pin 126 on trigger extension 108 and at the other to fixed pin 128 connected to a cover plate 130 in the lower arm 24.

When the secondary trigger 30 is retracted against the bias of spring 24 (moved horizontally to the right as viewed in FIG. 6), the interlock of its inclined flanges 118 and 120 with the flanges 100 and 102 carried by the stripper plate causes the stripper plate 80 to move downwardly from the position of FIG. 6 and the full line position of FIG. 5 to the dotted line position of FIG. 5, which in turn causes the foot 84 to strip the disposable tips 66 from the individual tip holders 50. The foot 84 engages the beads 67 on the tips to push the tips 66 off the holders. When the trigger 30 is released to the influence of spring 124, it returns to the position shown in FIG. 6 causing the stripper plate to rise and move its foot 84 to an elevated position so that new tips may be mounted on the holders 50.

The angle of inclination of the flanges 100, 102, 118 and 120 preferable is approximately 10° to the horizontal. This relationship of the flanges to the horizontal path of the secondary trigger 30 provides approximately a 7 to 1 mechanical advantage to the tip ejector so that even jammed tips may be forced off the tip holders 50 with one hand operation.

As shown in FIG. 5, cover plate 130 separates the lower arm 24 into back and front compartments 132 and 134. The stripper plate 80 and secondary trigger extension 108 lie in the front compartment 134 while the several lengths of flexible tubing 68 lie in the rear compartment 132. The cover plate 130 extends upwardly into the grip portion 26 of the housing to retain the portions of the tubing in that part of the housing in place. The cover plate prevents the tubing from interfering with the horizontal movement of the trigger 30 and the vertical movement of the stripper plate 80.

The upper arm 22 of housing 20 which is generally cylindrical in cross-section contains various assemblies for metering the quantity of fluid drawn into and dispensed from the pipetter by actuation of the primary trigger 28. The various parts of the assemblies in the upper arm 22 are shown in detail in FIGS. 6 to 10.

The rear portion of upper arm 22 (the end nearer grip portion 26 and rear wall of the housing) carries a cylindrical cylinder block 140 which is coaxially oriented within the upper arm 22 and is held in position by annular flanges 142 and 144 on the rear and forward ends, respectively, of the cylinder block. A shallow channel 146 is provided on the inner surfaces of the rear and front bodies 32 and 34, which channel receives the annular flange 144 to prevent the block 140 from moving axially in the upper arm 22. The cylinder block 140 may be fabricated of metal or other similar material. Twelve parallel cylinders 148 are arranged in a circular array in the cylinder block 140 with their axes parallel to and equidistantly spaced from the axis of the cylinder block. Each of the cylinders communicates with a passage 150 that extends through a nipple 151 carried on the rear face of the cylinder block. The nipples 151 telescope into the upper ends of the lengths of the tubing 68 connected to the tip holders 50. The forward end of each cylinder 148 is open through the front face of the cylinder block, and each open front end of the cylinders is chamfered as shown at 153 to facilitate insertion of the pistons 152 that slide axially in the cylinders. Each piston 152 carries an 0-ring 154 to form a seal between the piston and the cylinder wall. Each piston 152 in turn is carried by a piston rod 156 that extends forwardly to an annular flange 160 that forms part of the primary trigger mechanism 28. The piston rods 156 are secured to the flange 160 by screws 161.

A main guide rod 162 is coaxially mounted in the upper arm 22. The rear end 164 of rod 162 is anchored in the rear wall 166 of the housing at the parting line between the rear and front bodies 32 and 34.

The guide rod 162 has two main sections, namely, the smooth cylindrical portion 174 and the forward threaded portion 176. The threaded portion 176 screws into the internally threaded shaft 178 which is connected to an adjusting knob 172 by the screw 170. The guide rod rear portion 174 slidably supports a sleeve 180, which is molded of plastic and is integrally formed with the primary trigger 28 (see FIGS. 8 and 9). The sleeve 180 carries the annular flange 160 to which the piston rods 156 are connected by screws 161. In FIG. 7, it will be noted that a slot 183 is provided in the cylinder block 140 at the 6 o'clock position, and a flat plate 185 extends through the slot to connect the sleeve 180 to the finger grip portion of the trigger mechanism 28. The slot 183 enables the trigger mechanism to move on the guide rod 162 as is apparent in FIGS. 7-10. Thus, actuation of the primary trigger 28 causes the pistons 152 to move axially in the cylinders 148 of the cylinder block 140. As there are twelve cylinders 148 and twelve pistons 152 movable in them, there are 12 piston rods 156 connected to the annular flange 160 carried by the sleeve 180 of the trigger mechanism 28.

Figure 10:
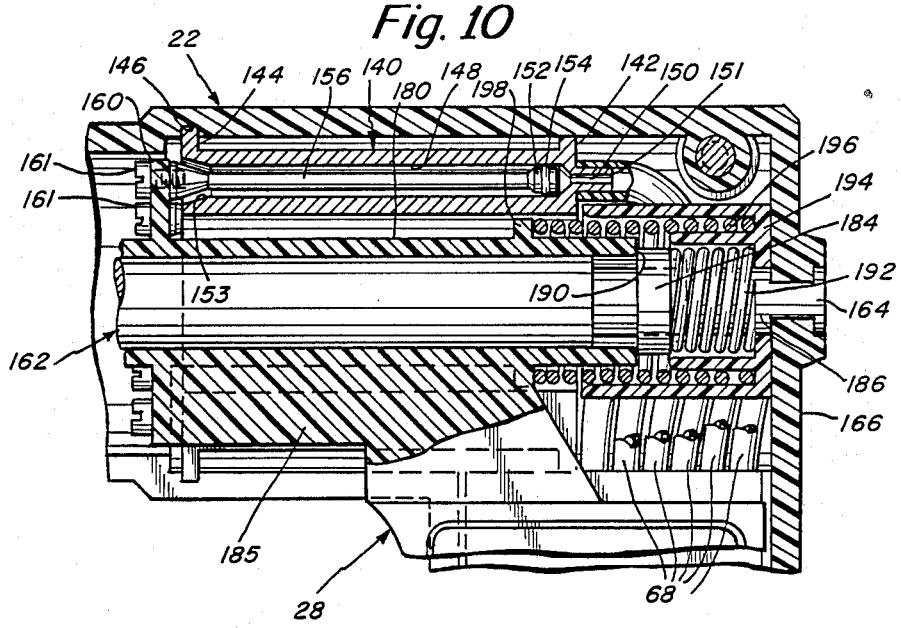
FIG. 10 is a fragmentary vertical cross-sectional view through the rear portion of the upper arm of the pipetter showing the yieldable stop assembly and with the trigger retracted to the blow-out position.

Fore and aft travel of sleeve 180 on the guide rod 162 are limited by the rear face 182 of shaft 178 that serves as one stop and by second stop 184 mounted on the rear portion 186 of the guide rod 162 that is of reduced diameter. In FIG. 8, the forward end 188 of sleeve 180 is shown to engage the stop 182 on shaft 178. In FIG. 9, sleeve 180 is shown with its rear end 190 engaging the second stop 184. The stop 184 is biased to the position shown in FIGS. 8 and 9 by coil spring 192 that is compressed between spring retainer 194 and the stop 184 itself. As shown in FIG. 10, the spring 192 may be compressed so as to move the second stop 184 rearwardly to afford the sleeve 180 additional rearward travel. When the sleeve 180 is moved to the rearward most position shown in FIG. 10, blow-out of the system occurs as is described more fully below in connection with the operation of the device.

Spring retainer 194 also supports the rear end of larger coil spring 196 which at its front end bears against a shoulder 198 on sleeve 180. Spring 196 urges the sleeve 180 to the forward position of FIG. 8 against the stop 182 established by shaft 178. To retract trigger 28 and move the sleeve 180 rearwardly on guide rod 162, the resistance of spring 196 must be overcome. When the rear end 190 of sleeve 180 engages stop 184, additional force must be exerted on the trigger to overcome the resistance of spring 192.

As described, shaft 178 serves as a stop to limit the forward travel of sleeve 180 on guide rod 162. The position of shaft 178 may be varied by rotating it by means of the adjusting knob 172 to which the sleeve is fixed by screw 170. When the shaft 178 turns, it moves either forwardly or rearwardly with respect to the upper arm 22 of housing 20. This travel of the shaft 178 is caused by engagement of its threaded bore 200 with the threaded section 176 of guide rod 162. Adjusting knob 172, shaft 178, rotatable barrel 38 and screw 170 together form a unitary structure during normal operation of the pipetter. Thus, when barrel 38 is rotated, or quick setting adjusting knob 172 is rotated, they both have the same effect upon the position of the shaft 178 in the upper arm 22 of housing 20. The threaded bore 200 and threaded section 176 of guide rod 162 together comprise a micrometer adjustment so as to allow the position of the stop 182 to be accurately monitored. It will be noted in FIG. 1 that a movable scale 202 is provided on the rotatable barrel or micrometer head 38 and an index line and fixed scale 204 are provided on the front body 34 to facilitate accurate metering for the pipetter. The front and rear bodies 34 and 32 of the housing together serve as the inner barrel of the micrometer. In order to zero the micrometer, screw 170 is loosened so as to allow the rotatable barrel 38 to turn independently of the knob 172 and shaft 178. It will be noted in FIGS. 8 and 9 that the forward portion 206 of barrel 38 is clamped between the flange 208 on shaft 178 and the inner wall 210 of knob 172 by means of the adjusting screw 170. When the screw is loosened, the clamping action of the flange 208 and wall 210 on the forward portion 206 of the barrel is reduced so as to allow the zeroing of the movable scale with respect to the index line 204 on front body 34.

It is apparent from the foregoing description that the position of stop 182 determines the maximum quantity of fluid that may be drawn into each cylinder 148 when the pipetter is loaded and of course how much is dispensed when the primary trigger 28 is retracted and the entire fluid volume is blown out of each cylinder. The fixed scale 204 on front body 34 along with the movable scale 202 indicates the setting of the stop 182 to achieve the selected volume. The scale 204 is shown calibrated in increments of 10 microliters, and the scale 202 on barrel 38 provides the unit adjustment within each 10 microliter increment.

Typically, the pipetter is used to load fluid simultaneously into 12 wells of a 96 well plate. Such a plate is suggested at P in FIG. 1. The technician using the instrument will initially apply the disposable tips 66 to the tip holders 50, which are available in bulk or in racks spaced for picking up twelve at one time. Next, the technician will use the micrometer to set the volume of fluid to be metered into each of the wells. FIG. 1 illustrates the micrometer positioned at the 190 microliter volume. The operator of course by turning the barrel 38 may set the volume at any desired quantity. Rotation of the barrel 38 (or adjusting knob 172) enables the operator to make the selection easily and accurately. Thereafter, one of several pipetting procedures may be followed. In the conventional procedure, after the adjustment has been made, the trigger 28 is squeezed so as to retract sleeve 180 to the position shown in FIG. 9 with the rear end 190 of the sleeve engaging second stop 184. Care should be taken not to exert so much pressure on the trigger 28 as to move the stop 184. Rather, the trigger should be squeezed to a position where the rear end 190 of the sleeve 180 just engages the stop 184 without compressing spring 192. Having done that, the technician next positions all of the tips 66 several millimeters beneath the surface of fluid in a reservoir (not shown) containing the particular fluid to be transferred. The trigger 28 is then released. When the trigger 28 is released, spring 196 acts upon the sleeve 180 to push it forward so that its front end engages the stop 182 on shaft 178. This action causes all of the pistons 152 to move from the position shown in FIG. 9 to that of FIG. 8 in their respective cylinders 148, which will cause the fluid in which the tips are submerged to be drawn upwardly through the tips 66 and the tip holders 50, tubing 68 and into the cylinders 148.

The pipetter is next moved to a position wherein the tips 66 are aligned with and perhaps extend into the row of wells in the plate P as suggested in FIG. 1. With the instrument in the position suggested, the technician again smoothly squeezes trigger 28, this time, however, beyond the position of FIG. 9 to that shown in FIG. 10, where pistons 152 are at the rearward most position in the cylinders 148. This causes total dispensing of the fluid drawn into the cylinders 148 without any fluid being left behind.

If the procedure warrants, the technician may then disconnect the tips 66 from the tip holders 50 by pulling the secondary trigger 30. That action will cause the stripper plate 80 to move downwardly as described above and cause the foot 84 of the stripper plate to bear against the upper rim 67 of each tip 66 and strip it from the tip holder. The operator may then apply new tips to the holders 50 merely by inserting the tapered lower ends of the tip holders into the next group of tips. This procedure may be repeated over and over again as desired.

A second procedure which may be more accurate for dispensing very small volumes of fluids and for liquids that easily foam or are of high viscosity is to pull the trigger to the position of FIG. 10 and then insert the tips several millimeters below the surface of the fluid to be transferred. Next the trigger is released to move to the position of FIG. 8. The fluid is then dispensed by pulling the trigger to the position of FIG. 9 so that sleeve 180 just engages stop 184. If multiple dispensing of identical volumes is required, the user may merely return the tips 66 to the reservoir while the trigger is in the position of FIG. 9, release the trigger to the spring 196 so that the position of FIG. 8 is again achieved, remove the pipetter and discharge the contents by again pressing the trigger to return the mechanism to the position of FIG. 9

From the foregoing description, the reader will appreciate the many advantages of the present invention. For example, because of the orientation of the metering cylinders 148 in a horizontal plane as opposed to a vertical plane, the overall height of the instrument is significantly reduced so that it may be used conveniently and comfortably under a laminar airflow hood commonly used in performing sterile laboratory procedures. The horizontal orientation of the cylinders reduces the instrument height by three inches or more. Another advantage of the present invention is that both the molded and machined parts are made of materials that may be autoclaved. The metal parts typically may be machined from aluminum or stainless steel, and the molded parts of the device may be made from such materials as ULTEM sold by General Electric Company or DELRIN made by Dupont Denemours E I & Co. It will also be appreciated that with the tip ejecting mechanism of the present invention, the pipetter can be operated with one hand. The secondary trigger 30 may be easily actuated by one or two fingers of the hand which holds the instrument. The inclined ramps which serve as cams to cause the stripper plate to move provide a 7 to 1 mechanical advantage. Furthermore, the flexible mountings for the tip holders provided by the 0-rings enable them to compensate for nonuniform positions of the tips before being picked up so that a secure grip may be achieved between each tip and holder.

The volumetric accuracy of the present invention is exceptionally high. The in line arrangement between the sleeve 180, pistons and piston rods 152 and 156, and the cylinders 158 provides uniformity from each of the channels of the pipette. Furthermore, the cylindrical pattern centered around the rigid precision machined stainless steel guide rod and its cooperating sleeve hold all of the parts in virtually perfect alignment.

Yet another advantage of the devices is that the micrometer head allows very accurate settings to be made of the position of stop 182. The micrometer configuration allows very fine divisions to be made of the range of quantities available, and the adjusting knob enables settings to be made quickly and allows the user to recalibrate the instrument to zero. Furthermore, the analog micrometer scale is a familiar arrangement to technicians so that it may be very easily used. Yet another important feature is that the product itself is human engineered so as to provide a design which prevents fatigue when the device is used repeatedly for hours. Finally, the arrangement of the parts and the handle design facilitates accurate aiming of the tips.

Having described this invention in detail, those skilled in the art will appreciate that numerous modifications may be made thereof without departing from the spirit of this invention. Therefore, it is not intended to limit the breadth of this invention to the single embodiment illustrated and described. Rather, it is intended that the scope of this invention be determined by the appended claims and their equivalents.

What is claimed is:

1. A multi-channel pipetter comprising
a U-shaped housing having generally parallel upper and lower arms and an interconnecting hand grip portion,
a plurality of parallel cylinders in a circular array disposed in the upper arm of the housing and a plurality of pistons movable in and out of respective ones of said plurality of cylinders,
a plurality of nozzles mounted on the lower arm of the housing and tubing connecting each of said plurality of nozzles to respective ones of said plurality of cylinders, said tubing extending from the lower arm to the upper arm through the grip portion,
a means including a trigger mechanism connected to each of said plurality of pistons and mounted on the grip portion for actuating said plurality of pistons through a stroke length to draw a quantity of fluid into and expel fluid from said plurality of cylinders via respective ones of said plurality of nozzles.

2. A multi-channel pipetter as defined in claim 1 wherein
a longitudinal axis of each of said plurality of cylinders is at right angles to a longitudinal axis of a respective one of said plurality of nozzles.

3. A multi-channel pipetter as defined in claim 1 wherein the upper arm has a longitudinal axis and said upper arm is generally horizontal when the pipetter is in an operative position,
a cylinder block coaxial with the longitudinal axis of the upper arm, each of said plurality of cylinders being in the block with a longitudinal axis of each said plurality of cylinders being parallel to the axis of the block,
a guide rod extending axially in the upper arm and coaxial with the block,
an actuatig sleeve forming part of the trigger mechanism and axially slidably mounted on the guide rod,
a plurality of piston rods attached to said plurality of pistons and extending out a first end of said plurality of cylinders and attached to the actuating sleeve, said tubing connecting a second end of each of said plurality of cylinders to respective ones of said plurality of nozzles,
means including a stop movable axially and rotationally on the guide rod for limiting axial travel of the actuating sleeve on the guide rod,
and spring means in the upper arm for biasing the actuating sleeve to a position wherein the stop is engaged by the sleeve,
said trigger mechanism being constructed and arranged when actuated to overcome the bias of the spring means to push said plurality of pistons into their respective cylinders and expel said quantity of fluid held therein through the respective tubing and said plurality of nozzles.

4. A multi-channel pipetter as defined in claim 1 wherein
said plurality of cylinders have longitudinal axes which are horizontal and said plurality of nozzles have longitudinal axes which are vertical.

5. A multi-channel pipetter as defined in claim 4 wherein
said plurality of nozzles each have an external tapered surface for receiving a removable nozzle tip.

and stripper means including a secondary trigger on the lower arm for removing said tips from said plurality of nozzles.

6. A multi-channel pipetter as defined in claim 5 wherein
said stripper means also indludes a plate operatively connected to the secondary trigger and movable along a path parallel to the axes of said plurality of nozzles and said secondary trigger moves substantially along a horizontal path perpendicular to the path of the plate.

7. A multi-channel pipetter as defined in claim 1 wherein means are disposed in the upper arm for adjusting said stroke length of said plurality of pistons to vary said quantity of fluid drawn into and expelled from said plurality of cylinders.

8. A multi-channel pipetter as defined in claim 7 wherein the means for adjusting said stroke length includes an actuating sleeve which is slidably mounted in the upper arm for movement along a path, connected to said plurality of pistons thereby forming part of the trigger mechanism,
a stop located in the upper arm and positioned in said path, and
an actuator on the upper arm connected to the stop for varying its position along said path.

9. A multi-channel pipetter as defined in claim 8 wherein
the acutator includes a threaded rod within the upper arm and a shaft threaded onto the rod, said shaft carrying the stop,
and a rotatable barrel disposed externally of the upper arm and connected to the shaft for rotating the shaft causing said rotatable barrel to move axially on the shaft to move the stop.

10. A multi-channel pipetter comprising
a housing having upper and lower compartments joined by a handgrip portion,
a row of a plurality of nozzles at the lower compartment disposed generally vertically when the pipetter is in an operative position,
a plurality of cylinders disposed in the upper compartment and having their respective axes arranged horizontally when the pipetter is disposed in an operative position.
tubing connecting an upper end of each of said plurality of nozzles to an end of a respective one of said plurality of cylinders and extending through the handgrip portion,
plurality of pistons in respective ones of said plurality of cylinders and connected to respective ones of a plurality of piston rods extending horizontally from a second end of each of said plurality of cylinders,
and actuating means movable along a path and connected to each of plurality of piston rods for moving said plurality of pistons within said plurality of cylinders to draw a quantity of fluid into said plurality of cylinders when said plurality of pistons are moved in one direction and to expel said quantity of fluid from said plurality of cylinders through said plurality of nozzles when said plurality of pistons are moved in a second direction.

11. A multi-channel pipetter as defined in claim 10 wherein
said actuating means includes a manually operated trigger mechanism mounted on the handgrip portion and connectd to each of said plurality of rods.

12. A multi-channel pipetter as defined in claim 11 wherein
adjusting means are diposed in the upper compartment of the housing for limiting travel of the actuating means along the path in one direction for metering the quantity of fluid which may be drawn into said plurality of cylinders.

13. A multi-channel pipetter as defined in claim 12 wherein
the adjusting means includes a stop in the path of said actuating means and a micrometer means connected to the stop for precisely positioning the stop for precision metering of said quantity of fluid.

14. A multi-channel pipetter as defined in claim 13 wherein
a second stop is disposed in the path for limiting the travel of the actuating means in the other direction,
and a spring engaging the second stop biasing that stop to a first position for establishing a starting position for the actuating means when fluid is to be drawn into said plurality of cylinders, said trigger mechanism being capable upon manual operation of overcoming the spring to move the second stop for ensuring complete discharge of said plurality of cylinders when the actuating means is moved from the first recited stop to the second stop.

15. A multi-channel pipetter comprising
a housing having upper and lower compartments,
a cylinder block mounted in the upper compartment and having a plurality of parallel cylinders arranged in a circular array, said plurality of cylinders having first and second ends and longitudinal axes,
a guide rod mounted in the upper compartment having a longitudinal axis parallel to the longitudinal axes of said plurality of cylinders,
a plurality of pistons slidable in respective ones of said plurality of cylinders and a plurality of piston rods connected to respective ones of said plurality of pistons,
a trigger mechanism disposed on a grip portion between the upper and lower compartments and including a sleeve slidably mounted on the guide rod, said sleeve connected to each of said plurality of piston rods and movable along a path as provided by the guide rod in the upper compartment for moving said plurality of pistons in said plurality of cylindrs toward and away from said first and second ends,
a plurality of nozzles in the lower compartment havig inner and outer ends and tubing connecting the inner ends to the first end of respective ones of said plurality of cylinders,
a first spring engaging the trigger mechanism for biasing said plurality of pistons toward respective ones of the second ends of said plurality of cylinders and causing said plurality of pistons to draw fluid into said plurality of cylinders when said plurality of pistons move from the first ends to the second ends and said plurality of nozzles of nozzles communicate with a fluid source, said trigger mechanism enabling an operator to move said plurality of pistons against the bias of the spring from the second ends to the first ends to expel fluid in said plurality of cylinders through ones of said plurality of respective ones of said plurality of nozzles,
and stop means in the upper housing disposed in the path of the sleeve for limiting travel of the sleeve and said plurality of pistons.

16. A multi-channel pipetter as defined in claim 15 wherein said stop means includes a first stop and a second spring for yieldably limiting the travel of said plurality of pistons toward the respective first ends of said plurality of cylinders,
said stop means also including a second stop for limiting travel of said plurality of pistons toward the respective second ends of said plurality of cylinders.

17. A multi-channel pipetter as defined in claim 16 wherein
adjusting means are disposed in the upper compartment and connected to the second stop for varying the position of the second stop.

18. A multi-channel pipetter as defined in claim 16 wherein
the adjusting means includes a threaded portion on the guide rod and an internally threaded shaft carrying the second stop and threaded onto the threaded portion of the guide rod for axial and rotational movement thereon,
a rotatable member mounted on the housing and connected to the shaft for rotating the shaft to move the second stop,
and calibrations on the rotatable member and the housing for indicating the volumetric intake for said plurality of cylinders as determined by the limit of travel of said plurality of pistons from the first to the second stop.

19. A pipetter comprising
a housing having an upper and lower compartment and an interconnecting handgrip portion,
a cylinder block in the upper compartment of said housing with at least one cylinder disposed therein,
at least one nozzle in the lower comparatment of said housing,the number of nozzles corresponding to the number of cylinders,
tubing connecting one end of each said at least one cylinder to a corresponding nozzle,
said at least one nozzle being oriented vertically in said housing and said at least one being oriented horizontally therein when the pipetter is in an operative position,
a plurality of pistons movable in respective ones of said at least one cylinder toward and away from said one end, each of said plurality of pistons drawing a quantity of fluid into a respective cylinder when the piston moves away from the said one end toward a second end and expelling said fluid from the respective cylinder when said piston moves away from the second end toward said one end,
an actuating mechanism connected to each of said plurality of pistons for moving said piston between the one end and the second end,
and adjustable means for varying travel of each of said plurality of pistons, 20. A pipetter as defined in claim 19 wherein
said at least one nozzle extending out of the lower compartment and having a downwardly tapered outer surface constructed and arranged to be inserted into a disposable tip to pick up and frictionally retain the tip on said at least one nozzle,
and flexible mounting means supporting said at least one nozzle in the lower compartment for enabling at least one nozzle to accommodate nonuniformity in the position of the tips to be picked up by said at least one nozzle.

* * * * *